United States Patent
Augthun et al.

(10) Patent No.: US 6,840,769 B2
(45) Date of Patent: Jan. 11, 2005

(54) MEDICAL IMPLANT

(75) Inventors: Michael Augthun, Aachen (DE); Manfred Peters, Wolfenbüttel (DE); Klaus Haselhuhn, Aachen (DE); Hubertus Spiekermann, Haan (DE)

(73) Assignee: Heraeus Kulzer GmbH & Co. KG, Hanau (DE)

( * ) Notice: Subject to any disclaimer, the term of this patent is extended or adjusted under 35 U.S.C. 154(b) by 0 days.

(21) Appl. No.: 10/257,926

(22) PCT Filed: Apr. 6, 2001

(86) PCT No.: PCT/EP01/03948

§ 371 (c)(1),
(2), (4) Date: Apr. 14, 2003

(87) PCT Pub. No.: WO01/80768

PCT Pub. Date: Nov. 1, 2001

(65) Prior Publication Data

US 2003/0157459 A1 Aug. 21, 2003

(30) Foreign Application Priority Data

Apr. 19, 2000 (DE) .......................... 100 19 338

(51) Int. Cl.[7] ................................................ A61C 8/00
(52) U.S. Cl. ..................................................... 433/173
(58) Field of Search ............................... 433/172, 173, 433/174, 175, 176

(56) References Cited

U.S. PATENT DOCUMENTS

| | | | | |
|---|---|---|---|---|
| 5,030,095 A | * | 7/1991 | Niznick | 433/173 |
| 5,197,881 A | | 3/1993 | Chalifoux | 433/173 |
| 5,246,370 A | | 9/1993 | Coatoam | 433/173 |
| 5,695,335 A | * | 12/1997 | Haas et al. | 433/173 |
| 5,961,328 A | | 10/1999 | Somborac et al. | 433/173 |
| 6,273,720 B1 | * | 8/2001 | Spalten | 433/173 |
| 6,358,052 B1 | * | 3/2002 | Lustig et al. | 433/174 |

FOREIGN PATENT DOCUMENTS

| | | | |
|---|---|---|---|
| DE | 32 41 963 C1 | 4/1984 | ............ A61C/8/00 |
| DE | 33 00 764 A1 | 7/1984 | ............ A61C/8/00 |
| DE | 35 33 395 A1 | 5/1986 | ............ A61C/8/00 |
| DE | 36 11 139 A1 | 10/1986 | ............ A61C/8/00 |
| DE | 41 27 839 A1 | 3/1992 | ............ A61C/8/00 |
| DE | 296 05 296 U1 | 7/1996 | ............ A61C/8/00 |
| WO | WO 99/29255 | 6/1999 | ............ A61C/8/00 |
| WO | WO 00/64384 | 11/2000 | ............ A61F/2/36 |

* cited by examiner

Primary Examiner—Cary E. O'Connor
(74) Attorney, Agent, or Firm—Norris McLaughlin & Marcus PA

(57) ABSTRACT

Implant (1) for receiving the connecting bridge (17, 17', 17") of a medical device, comprising a longitudinal axis (9), a distal end (3) and a proximal end (4), whereby a receiving recess (10) for the connecting bridge (17, 17', 17") extends therefrom inside the implant (1), wherein the implant (1) can be connected on its outer surface area to the inner surface area of a receiving bore hole in a bone by force or adaptation, and whereby the connecting bridge (17, 17', 17"), which is adapted to the receiving recess (10), can be anchored through clamping, shrinkage, adhesion or cementing. The anchored medical device rests on a contact surface (18) of the top (16) protruding radially outward in its cross-section beyond the cross-section of the receiving recess (10) on the proximal end (4) of the implant (1) across the entire surface against an allocated contact surface (5) of the implant (1) on its proximal end (4). In order to accomplish this the medical device can be easily assembled while simultaneously ensuring a high torsional safety as well as even force transmission between the implant and the medical device it is suggested that extending from the proximal end (4) of the implant (1) the receiving recess (10) contain a cylindrical section (10Z), which is followed by a section (10V) that is tapered in its cross-section, and that extending from the top (16) of the medical device the connecting bridge (17, 17', 17") also contain a cylindrical section (17Z), which is followed by a section (17V) that is tapered in its cross-section.

14 Claims, 12 Drawing Sheets

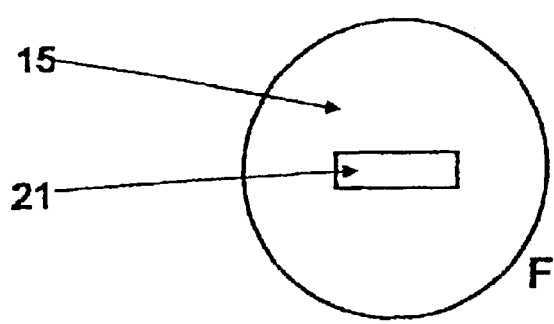
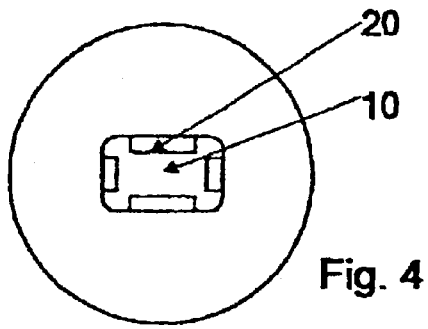
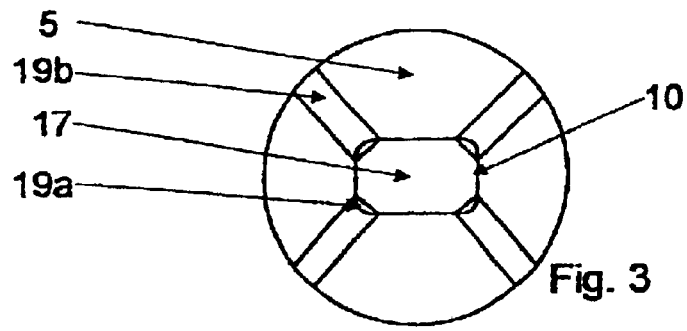
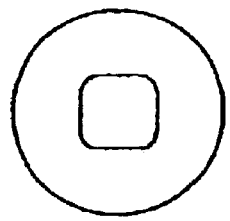
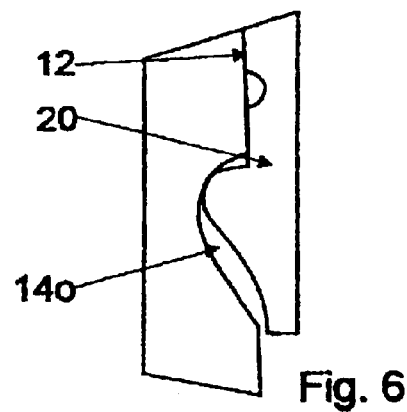

MEDICAL IMPLANT

This application is a 371 of PCT/EP01/03948, filed on Apr. 6, 2001.

The invention concerns an implant which will house the connecting bridge of a medical device and is composed of a longitudinal axis and a distal and proximal end, from which a receiving recess for the connecting bridge extends into the implant, making it possible for the implant to be connected by force on its outer surface, or adapted to the inner surface of a receiving bore hole in the bone of a human or animal, in that the connecting bridge, which is adapted to the receiving recess, can be anchored either by clamping, shrinking, adhesion or cementing, and once anchored, the medical device rests against the contact surface of the top which protrudes radially outward in its cross-section beyond the cross-section of the receiving recess on the proximal end of the implant, crossing the entire surface against an allocated contact surface of the implant on its proximal end if at least in one section of the outer contour of the cross-section of the receiving recess is not circular.

Such implant systems are, for example, widely known in dental medicine. In this case, the medical device to be received, will, e.g., be formed by a dental implant, cap or gingiva shaper. The implant is, for example, screwed into the jawbone.

An implant system of the above-described kind is known for example from U.S. Pat. No. 5,961,328. The connecting bridge of the medical device and the receiving recess of the implant are joined based on the key-lock principle, wherein a non-rotational joint is reached With the help of locking elements protruding radially beyond the connecting bridge, where these elements in the inserted state of the medical device mesh with the adapted recesses in the head portion of the implant. Extending from the proximal end of the implant, the receiving recess initially contains a conical section, which is followed by a cylindrical section, the cross-section of which corresponds to the cross-section at the end of the conical section. The connecting bridge of the medical device to be inserted into the receiving recess exhibits a tapered shape in its cross-section in the direction of its distal end, whereby the outer contour of the connecting bridge is concave in the longitudinal section and contains a saw-tooth surface structure. The cross-section of the connecting bridge however is not circular, but rather in comparison to a rotationally symmetrical design a longitudinal strip is missing on one side so that a plane section of the outer surface area is created, which runs parallel to the longitudinal axis of the connecting bridge.

The production of this familiar implant system is for one very complex and therefore expensive, and on the other hand the way the way forces are introduced into the conical section following the head portion of the medical device is not optimal. Due to the tapered cross-section, the absorption of forces, which arise especially with single-sided stress of the medical device and are directed lateral to the longitudinal axis of the connecting bridge, can possibly be limited, leading in the most unfavorable case to tilt movements of the medical device.

The dental implant known from WO 99/29255 consists of a connecting bridge with a bottom portion, a central portion, an upper part and a crown slid onto the top. The dental implant is inserted in its entirety with its conical bottom portion into an identical conical receiving bore hole that has been adapted to it in an implant, which must first have been inserted into the jawbone and have healed sufficiently. When joining the connecting bridge and the receiving bore hole, the principle of a clamping cone is applied. Although the possibility of torsion of the dental implant about the longitudinal axis of the connecting bridge allows the angular position of the dental implant to be adapted exactly in relation to a rotation about its vertical axis when inserted, it has the particular disadvantage that with greater stress, sufficient torsion safety of the dental implant cannot be guaranteed for the implant system.

An alternative to the described implant system a screw connection between the replacement tooth and the implant is the most widely used type of connection and is characterized by being easily reversible. The disadvantage here, however, is the large amount of time that is required for screwing in the fastening screws—especially with a larger number of dental implants—as well as the frequently unsatisfactory durability of such a system. Due to the manufacturing process, no threads of the screw connection ever exhibit the same wear behavior, which, in isolated sections, results in elevated, and in other sections, reduced force or moment transmission. This creates undefined stress conditions, which can result in undesirable deformations and tension peaks. This in turn leads to damage to the screw connection or to excessive stress on the connection between the implant and bone, which in the worst case can cause a total loss of the implant.

The invention's purpose is to present an implant system, where the connection between the medical device and the implant can be prepared in a simple manner, and the connection should also be characterized by the ability to introduce even force across a large surface as along with torsion safety.

Proceeding from an implant of the above-described kind, this task is resolved pursuant to the invention through the fact that the receiving recess, extending from the proximal end of the implant, exhibits a cylindrical section, which is followed by a section that is tapered in its cross-section, and that the connecting bridge, extending from the top of the medical device, also contains a cylindrical section, which is followed by a section that is tapered in its cross-section.

The fact that contact with the contact surfaces occurs across the entire surface causes force to be introduced evenly from the medical device into the implant, avoiding tension peaks and thus excessive material stress and damage, particularly as the cylindrical section of the connecting bridge linked with the adapted cylindrical section of the receiving recess affects safe fastening, where even an extreme lateral force introduction into the medical device does not lead to tensile force components in the interface between the medical device and the inner surface area of the implant. The implant pursuant to the invention therefore offers an especially high degree of safety against it detaching and falling out, independent of the fact whether the medical device is shrunk in, glued in or cemented in.

The non-circular cross-section, which can take on the form, for example, of a (rounded-off) polygon (triangle, square, pentagon, etc.) or an ellipse or an oval or any random other such shape, prevents a torsion of the connecting bridge of the medical device about its longitudinal axis. The clearly defined angular position of the medical device in relation to its rotation about its vertical axis additionally eliminates the difficult adjustment of the medical device's position during the insertion process. The actual connection between the implant and the connecting bridge occurs through clamping, shrinkage, adhesion or cementing.

Pursuant to one embodiment of the invention, the length of the cylindrical section of the connecting bridge, measured in the direction of the longitudinal axis of the implant, should be slightly smaller than the length of the cylindrical section of the receiving recess, also measured in the direction of the longitudinal axis of the implant. This provides a safe contact with the contact surfaces of the medical device on one hand and of the implant on the other hand, which is essential for an even application of forces across a large surface. The difference in length should be such that, while taking the production tolerances of the individual elements into consideration, even in the most unfavorable case, contact in the area of the contact surfaces is always ensured. The difference in length, however, should not be selected too high in order to avoid unnecessarily large gaps between the connecting bridge and the receiving recess in the area of the tapering cross-sections.

In a particularly preferred embodiment the contact surface is circular and runs in a plane vertical to the longitudinal axis of the implant. With the help of such a design, the efforts required during the production of the implant can be kept particularly low.

To avoid a pressure build-up that may impair the insertion motion during insertion of the connecting bridge into the receiving recess, between the connecting bridge in its anchored state and the wall of the receiving recess, at least one ventilation duct is included which extends from a distal end face of the connecting bridge to the proximal end of the implant.

It is particularly beneficial when the contact surface of the implant contains at least one ventilation groove which extends from a ventilation duct to the surface area of the implant. Thus, a completely unimpaired outflow of the air that is displaced by the connecting bridge is guaranteed.

It is useful to size the connecting bridge in comparison to the receiving bore hole such that the connecting bridge can always be inserted so far into the receiving recess that the contact surface of its top rests across its entire surface against the contact surface of the implant.

One development of the invented implant consists of a design where the wall of the receiving recess contains a plurality of ring grooves, which run in the planes vertical to the longitudinal axis of the implant, respectively, or contains a helical groove. The ring grooves and/or the helical groove ensure on one hand that the assembly process, especially in its last phase, is facilitated. Above all, it prevents stress of the surfaces placed against each other and accomplishes better guidance of the connecting bridge. Additionally, when fixating the connecting bridge with the help of adhesive, adhesive rings etc., in the ring grooves and/or in the helical groove a helical adhesive bead is created, via which axial forces can be absorbed.

Developing the invention further, it is suggested that the wall of the receiving recess be equipped with at least one indentation, with which an elastic clip element of a medical device, i.e. for example a cap, a gingiva shaper, an impression rod and/or a temporary replacement tooth can positively engage. This way all components that have to be connected only temporarily with the implant can be inserted in a simple manner into the receiving recess and thus be connected with the implant in an exactly predetermined position. The clip element creates a positive connection that can be eliminated again by appropriate axial forces; for this purpose the clips are beneficially rounded off in order to enable non-damaging separation. During the transitional period, the transmission of forces takes place via the end faces. The time that is required for preparing the connection between components that are used only temporarily and the implant is drastically reduced, which expresses itself in a considerably gain in time especially for the simultaneous use of a plurality of implants.

In a preferred embodiment of the invented implant, the cross-section of the receiving recess takes on the shape of a rounded-off rectangle in the vicinity of the proximal end of the implant and the shape of a rounded-off square in the vicinity of its base, wherein the transition between the above-mentioned cross-sectional shapes occurs smoothly. It is useful when the shorter edge length of the rectangle corresponds to the edge length of the square.

Pursuant to the invention, a medical device is suggested which has one contact surface of a head portion protruding radially outward in its cross-section beyond the cross-section of the receiving recess on the proximal end of the implant resting across the entire surface against an allocated contact surface of the implant on its proximal end and where the outer contour of the cross-section of the receiving recess at least in one section is not circular. This provides torsional safety in a simple manner and also enables greater moments of torsion to be absorbed without placing the connection at risk. It thus provides the opportunity of inserting the implant, e.g. together with a pre-assembled cap or a gingiva shaper into the bone.

In a beneficial embodiment, the connecting bridge exhibits in the vicinity of its proximal end a cross-section in the shape of a rectangle, the corners of which are rounded-off or broken more than those of the rectangle of the cross-section of the receiving recess in the position that is allocated in the anchored state, and exhibits in the vicinity of its distal end a cross-section in the shape of a rounded-off square, the corners of which are rounded-off more than those of the square of the cross-section of the receiving recess in the position that is allocated to the anchored state.

Furthermore it is suggested that the distal end of the connecting bridge should contain at least one axially protruding clip element, which in the assembled state can be positively engaged with an indentation in the receiving recess of the implant. The time required during assembly can thus be reduced considerably compared to screw connections and/or temporary adhesive or cement connections.

The positive connection through the clip element can be eliminated in a simple manner if a section, which in the installed state is located outside the receiving recess, contains in its surface area at least two opposing indentations. In these indentations, hook-shaped contact elements of a tool shaped like tongs, can, for example, be inserted, to allow a clipped-on cap, a clipped-on gingiva shaper, impression rod and/or temporary replacement tooth to be easily removed again from the implant by applying the appropriate axial forces.

Establishing a positive connection between the tool used to remove the cap, the gingiva shaper, the impression rod and/or the temporary replacement tooth can be simplified if the indentations form a ring groove with a V-shaped cross-section.

Developing the invention further, a final replacement tooth can be such that the surface area of the connecting bridge contains a plurality of ring grooves which run in a plane vertical to the longitudinal axis of the connecting bridge, respectively, and in the anchored state of the replacement tooth correspond to the ring grooves in the wall of the receiving recess.

BRIEF DESCRIPTION OF THE DRAWINGS

The invention is explained in more detail in the following based on one example, which is shown in the drawing.

It shows:

FIG. 2 Top view onto the cap;

FIG. 3 Top view onto the implant upon removal of the cap;

FIG. 4 Cross-sectional view along line IV—IV through the implant pursuant to FIG. 1;

FIG. 5 Cross-sectional view along line V—V through the implant pursuant to FIG. 1;

FIG. 6 Enlarged section of the engagement area of a clip element;

FIGS. 1 through 5 reveal an implant 1 consisting of titanium, which has a roughly conical outer base shape and on its outer surface area contains an outer thread 2. Implant 1 contains a rounded-off distal end 3 and a proximal end 4, which is formed by a largely circular contact surface 5. In a section 6 following the contact surface 5, the implant exhibits on its outside a cylindrical shape with a high-polished surface area 7. In a thread area 8 that follows the implant 1 has a conical design. Starting from the contact surface 5, parallel to the longitudinal axis 9 of the implant 1, a receiving recess 10 extends, which runs across the entire length of the section 6 as well as a portion of the length of the threaded section 8.

Figure 7:
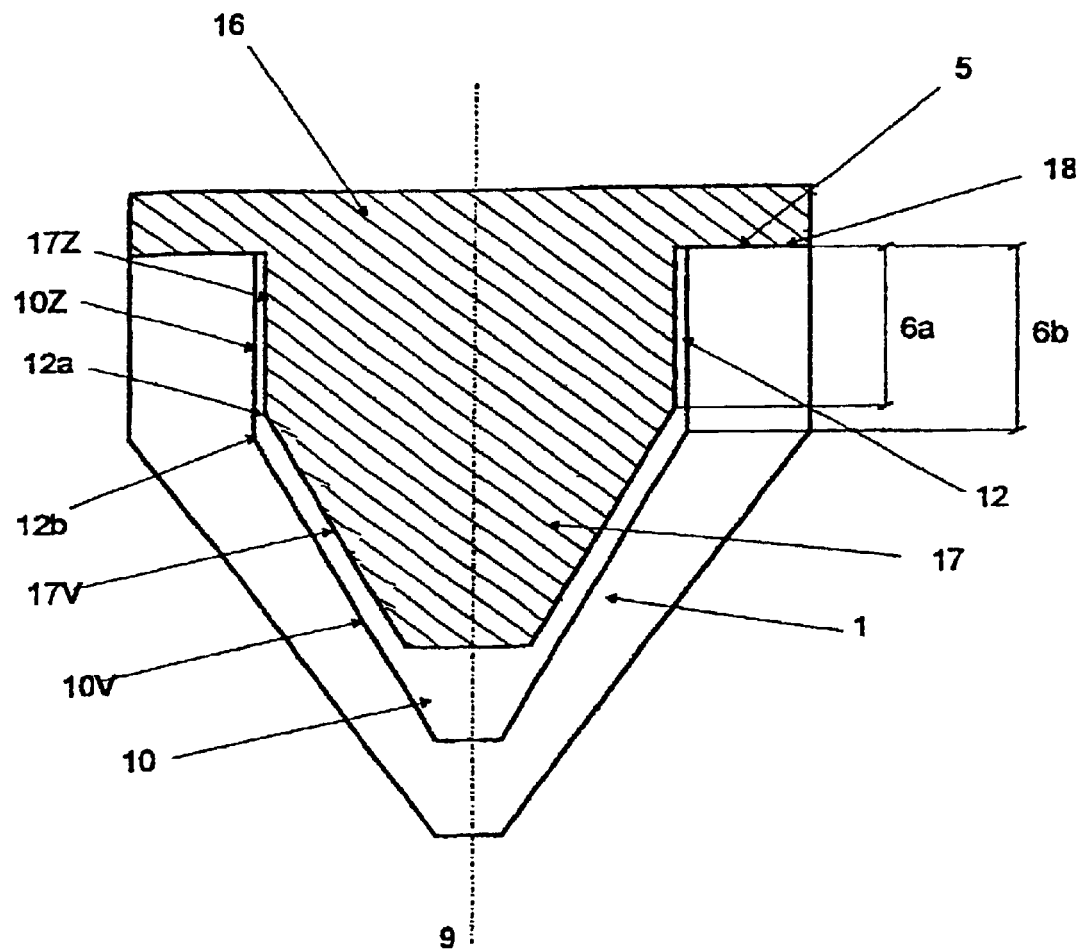
FIG. 7 Enlarged and diagrammatic section of the differing start of the cross-sectional taper of the implant and the connecting bridge.

The diagrammatic depiction pursuant to FIG. 7 shows that extending from the proximal end 4 of the implant 1 the receiving recess 10 first contains a cylindrical section 10Z, which is followed by a section 10V that is tapered in its cross-section. Adapted to this feature, extending from the head portion 16, the connecting bridge 17 of a replacement tooth to be inserted initially also exhibits a cylindrical section 17Z, the diameter of which is slightly smaller than the diameter of the receiving recess 10 in its cylindrical section 10Z. The cylindrical section 17Z of the connecting bridge 17 is followed by a section 17V, which is tapered in its cross-section. Since the length 6a of the cylindrical section 17Z of the connecting bridge 17 is dimensioned slightly less than the length 6b of the cylindrical section 10Z of the receiving recess 10, it is impossible for the connecting bridge 17 to rest against the wall 12 of the receiving recess 10 in the area of the tapering sections 10V, 17V. This kind of adaptation of the components rather ensures that the contact surfaces 5 and 18 always rest there across their entire surface at the proximal end of the implant 1. The difference between the lengths 6b and 6a, i.e. the axial distance between the peripheral edges 12a on the connecting bridge 17 and 12b on the receiving recess 10 of the implant 1, is dimensioned such that even in the most unfavorable case of production tolerances always a minimum gap is maintained in the sections 10V and 17V. The difference in length should otherwise be kept as small as possible in order to keep the gap in the area of the tapering sections 10V and 17V small.

As FIGS. 3 and 7 show, the cross-section of the receiving recess 10 takes on the shape of a rounded-off rectangle in the area of the cylindrical section 10Z. Starting with the threaded area 8, the cross-section of the receiving recess 10 tapers continuously in a subsequent section 10V so that on the base 11 of the receiving recess 10 the cross-section has the shape of a rounded-off square (see FIG. 5). In the threaded area 8, the transition from the rounded-off rectangular to the rounded-off square cross-sectional shape occurs continuously and smoothly.

Figure 1:
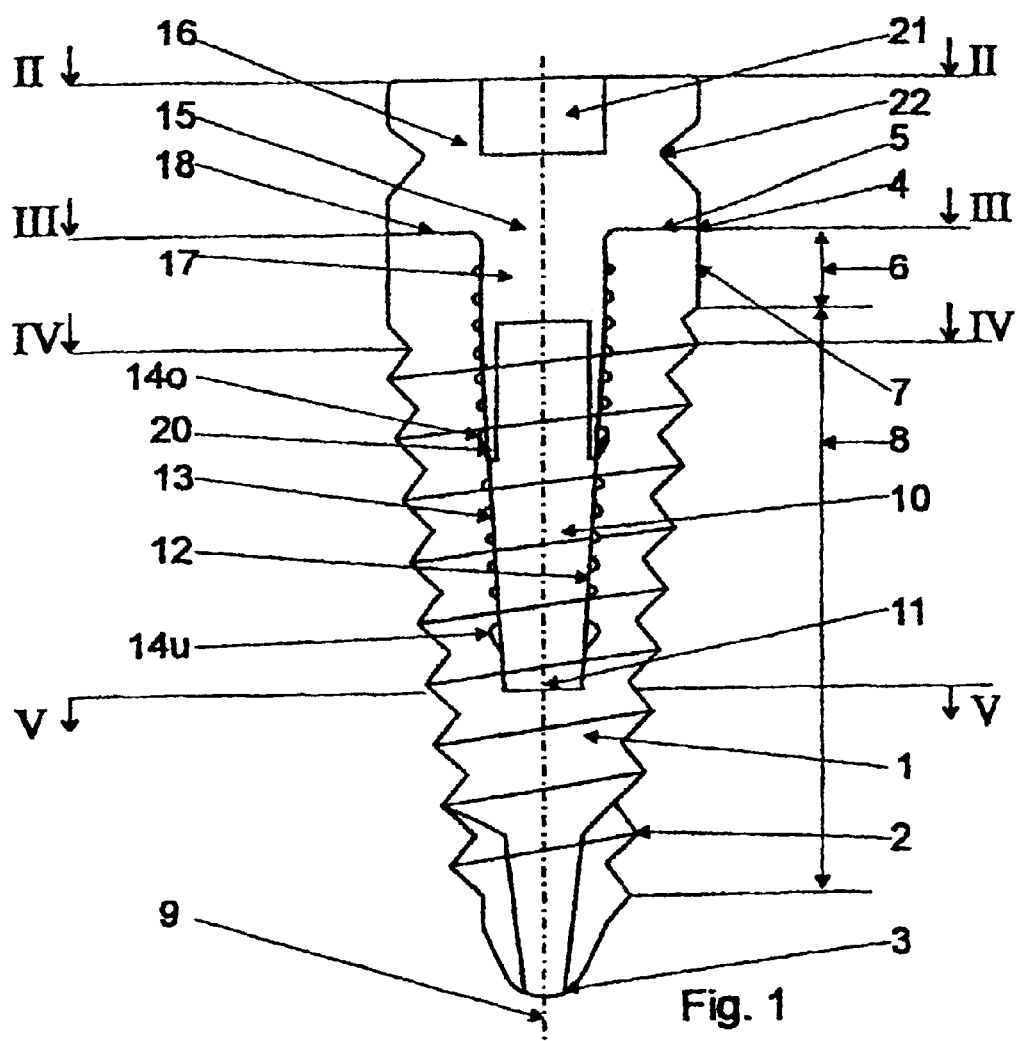
FIG. 1 An implant with a clipped-on cap in a longitudinal sectional view.

As particularly shown in FIG. 1, the wall 12 of the receiving recess 10 contains a plurality of ring grooves 13, which are aligned vertical to the longitudinal axis 9. Furthermore the wall 12 is equipped with an upper and a lower clip groove 14o and 14u, the function of which is explained below based on FIG. 6.

Implant 1 depicted in FIG. 1 is inserted in a cap 15, consisting of a roughly cylindrical head portion 16 and a coaxially thereto aligned connecting bridge 17, which extends in the receiving recess 10. A contact surface 18 of the head portion 16 rests positively on the contact surface 5 of the implant 1.

As FIG. 3 reveals, the connecting bridge 17 has in its upper section a roughly rectangular cross-section, wherein the corner areas are broken in such a way that in the rounded-off areas of the cross-section of the receiving recess 10 between the connecting bridge 17 and the wall 12 of the receiving recess 10 four ventilation ducts 19a are formed. Air displaced when inserting the connecting bridge 17 in the receiving recess 10 can thus flow out upward without causing a pressure build-up that would impair the assembly process, wherein the air can escape to the outside through four radially outward extending ventilation grooves 19b, which are incorporated in the end face 5 of the implant and communicate with the ventilation ducts 19a.

Since the cap remains on the implant 1 only temporarily after implantation, it is connected with implant 1 only through four clip elements 20, which engage with the clip groove 14o. Instead of the engagement of the clip elements 20 in the upper clip groove 14o shown in FIG. 1, engagement in the lower clip groove 14u is also possible with an appropriately extended connecting bridge 17.

Cap 15 is already inserted into implant 1 by the implant manufacturer and upon preparation of an appropriate bore in the bone serves the purpose of screwing implant 1 in with the help of a screwdriver, which engages with the slot 21 shown in FIG. 2. Due to the roughly rectangular cross-section of the connecting bridge 17 and the adapted receiving recess 10, the introduction of moments of torsion into the implant 1 is possible via the cap 15. Upon implantation, the cap 15 remains on the implant 1 in order to protect also the receiving recess 10 from outside contamination.

Figure 8:
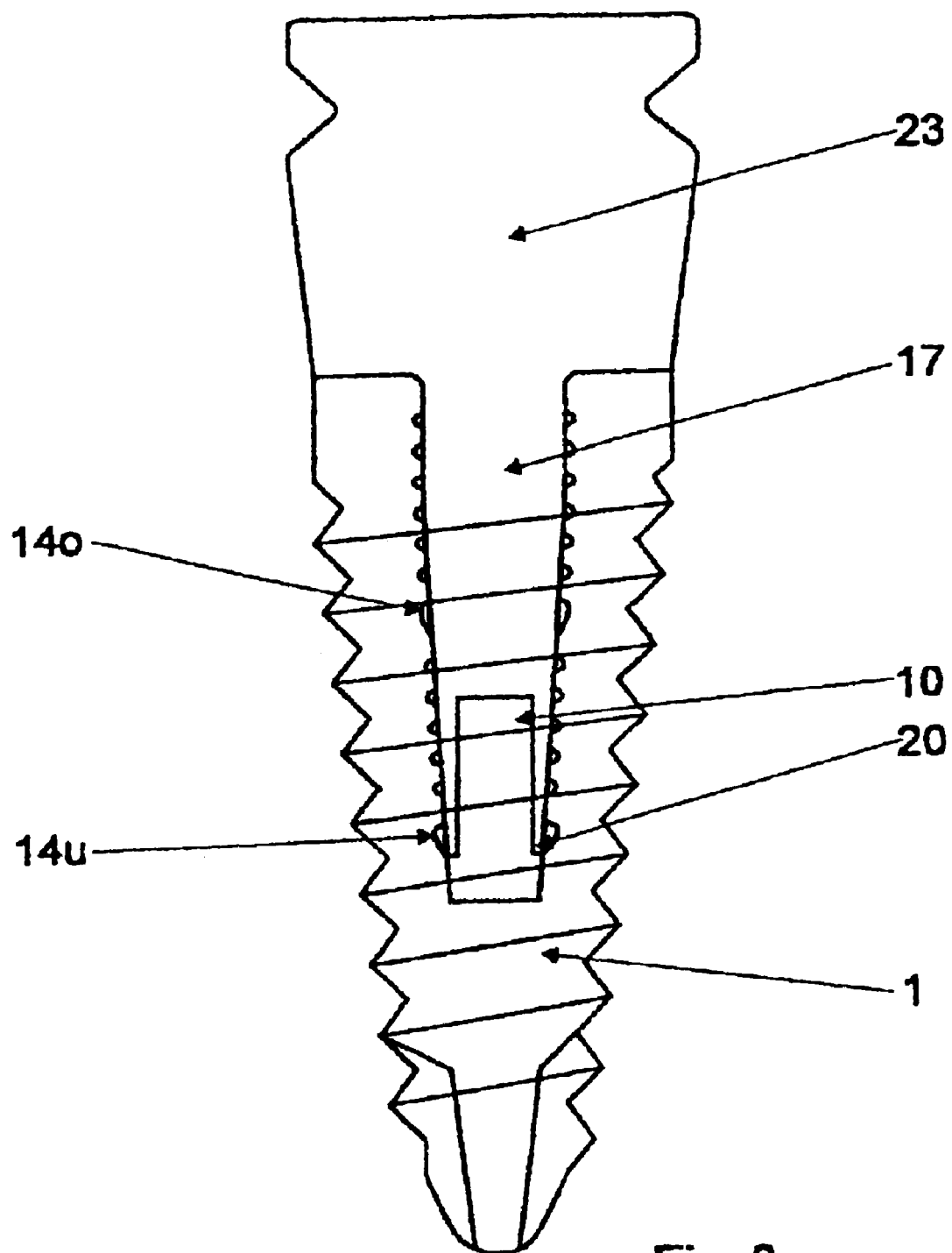
FIG. 8 As in FIG. 1, however with clipped-on gingiva shaper.

Approximately three to six months after insertion of the implant in the jaw bone, the healing process will be completed far enough to be able to open up the mucous membrane covering Cap 15 in a second surgery. Cap 15 is removed, which is accomplished by reaching into a V-shaped ring groove 22 in the head portion 16 with the help of a tool in the shape of tongs and removing the entire cap 15 upward from the implant 1 with a slight jerk in the axial direction. Into the receiving recess 10 of the implant 1 now a connecting bridge 17 of a gingiva shaper 23 is inserted, as shown in FIG. 8. The fastening principle is the same as with the cap 15. As an example, FIG. 8 shows that the clip elements 20 of the gingiva shaper 23 snap into the lower ring groove 14u. Similarly feasible however is a gingiva shaper 23, where the clip elements engage with the upper ring groove 14o.

Figure 9:
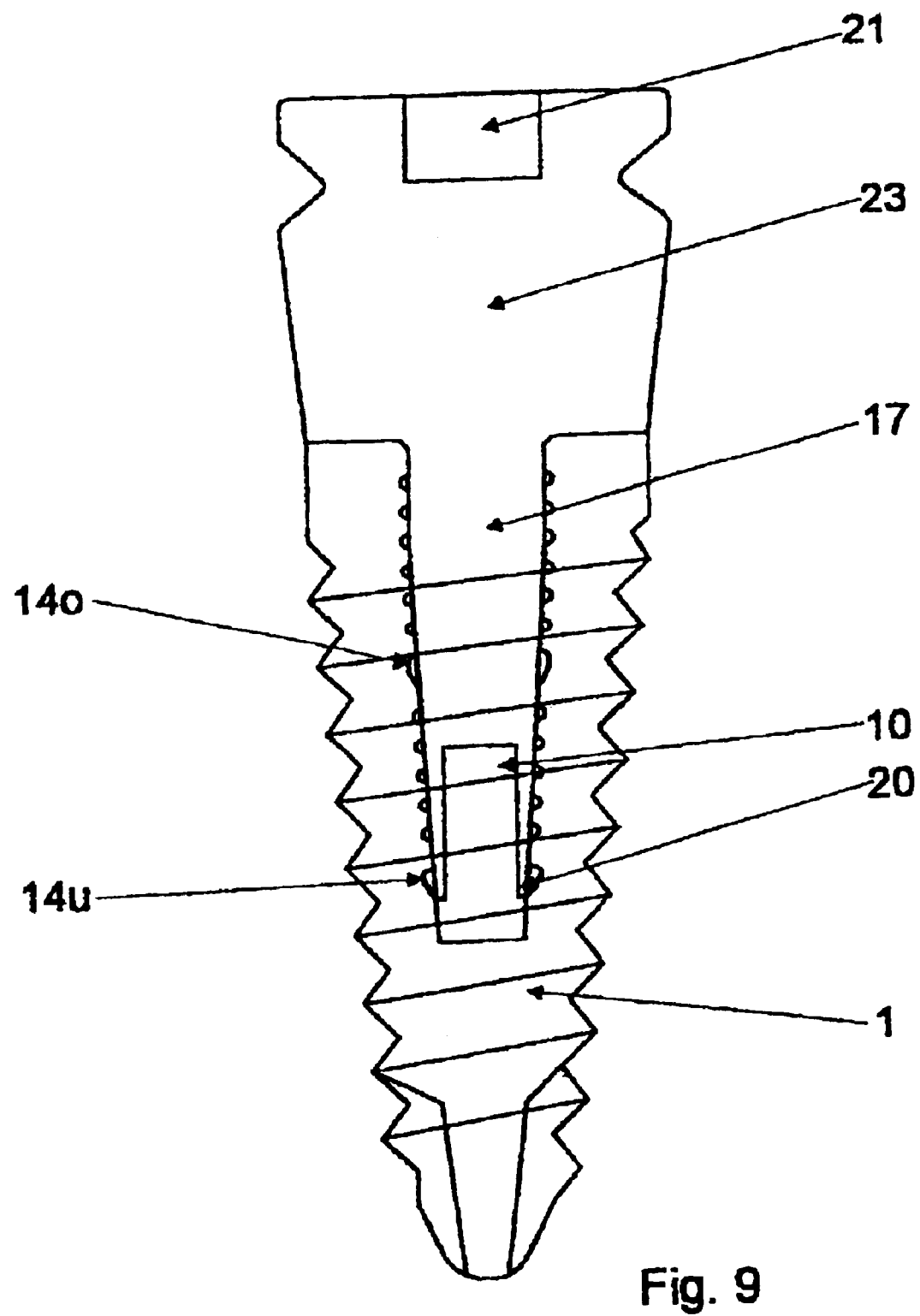
FIG. 9 As in FIG. 8, however with a slot in the gingiva shaper for transgingival healing.

FIG. 9 shows a gingiva shaper with a slot, which is employed for transgingival healing of the implant.

Figure 10:
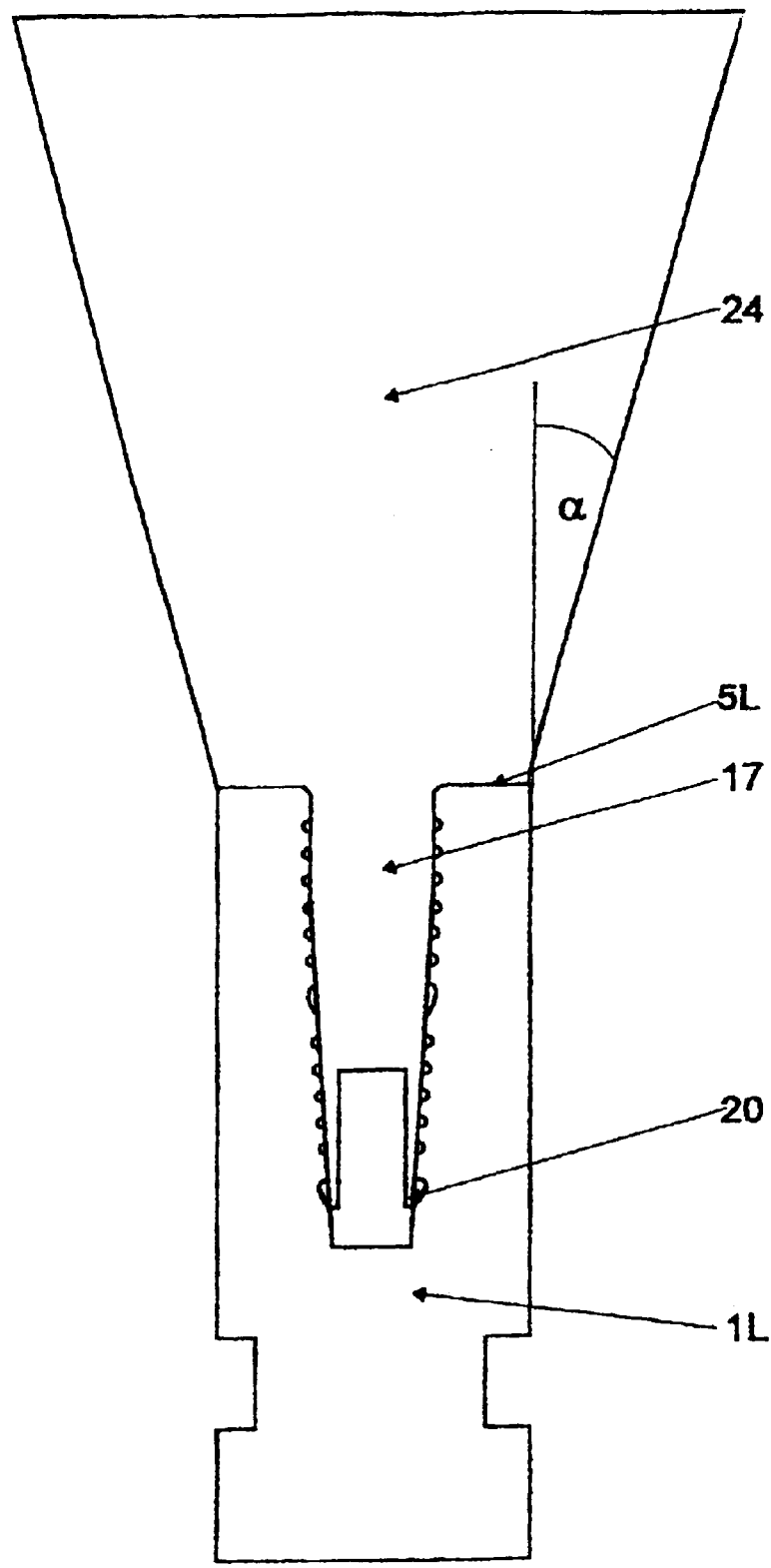
FIG. 10 Blank for a temporary replacement tooth in a lab implant.

FIG. 10 depicts a lab implant 1L, into which a blank 24 of a temporary replacement tooth has been inserted, also with the help of a connecting bridge 17. The blank 24 is truncated and expands, starting from the end face 5L of the lab implant 1L, at an angle α of 15°. This way, slanted positions of the implant 1 or 1L in relation to adjacent teeth can be compensated for in wide angular ranges in all directions. The connecting bridge 17 of the blank 24 also contains clip elements 20, which ensure uncomplicated fixation and removal of the blank 24.

Figure 11:
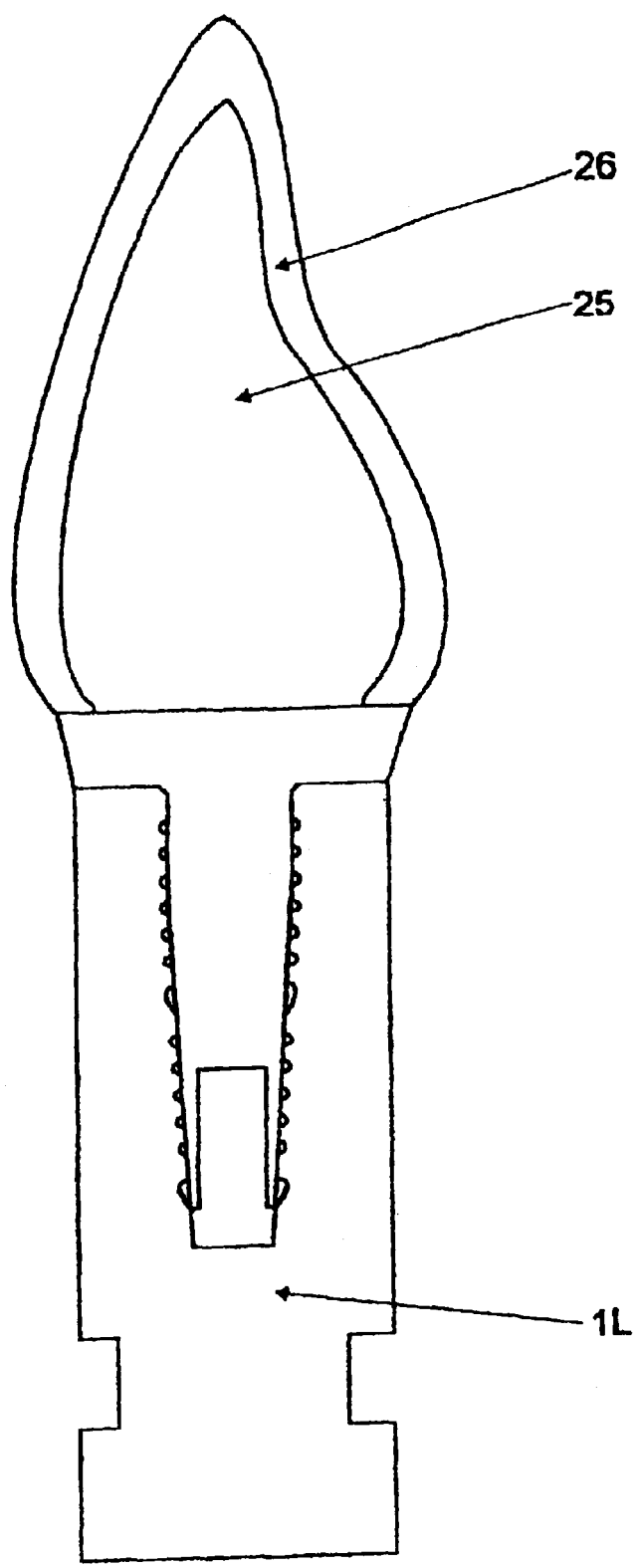
FIG. 11 As in FIG. 10, however of a finished temporary replacement tooth.

FIG. 11 shows a finished temporary replacement tooth 25, which was prepared by cutting the blank 24 in a dental laboratory. Onto the ground blank an outer ceramic layer 26 has been burned.

Figure 12:
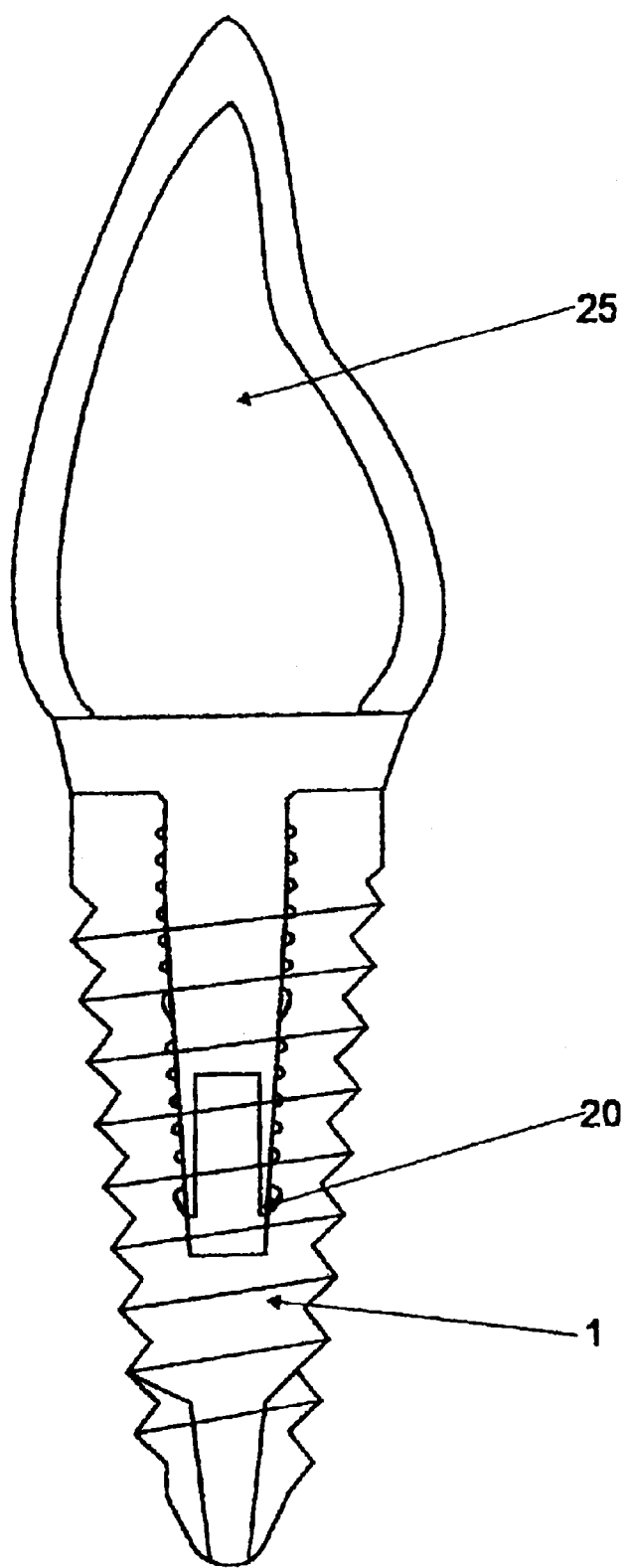
FIG. 12 As in FIG. 11, however in the implant pursuant to the invention.

The finished temporary replacement tooth 25 can subsequently be inserted on the patient in the implant 1 and be fixated there with the help of the clip elements 20 until the patient can be provided with the final replacement tooth 28 (FIG. 12).

Figure 13:
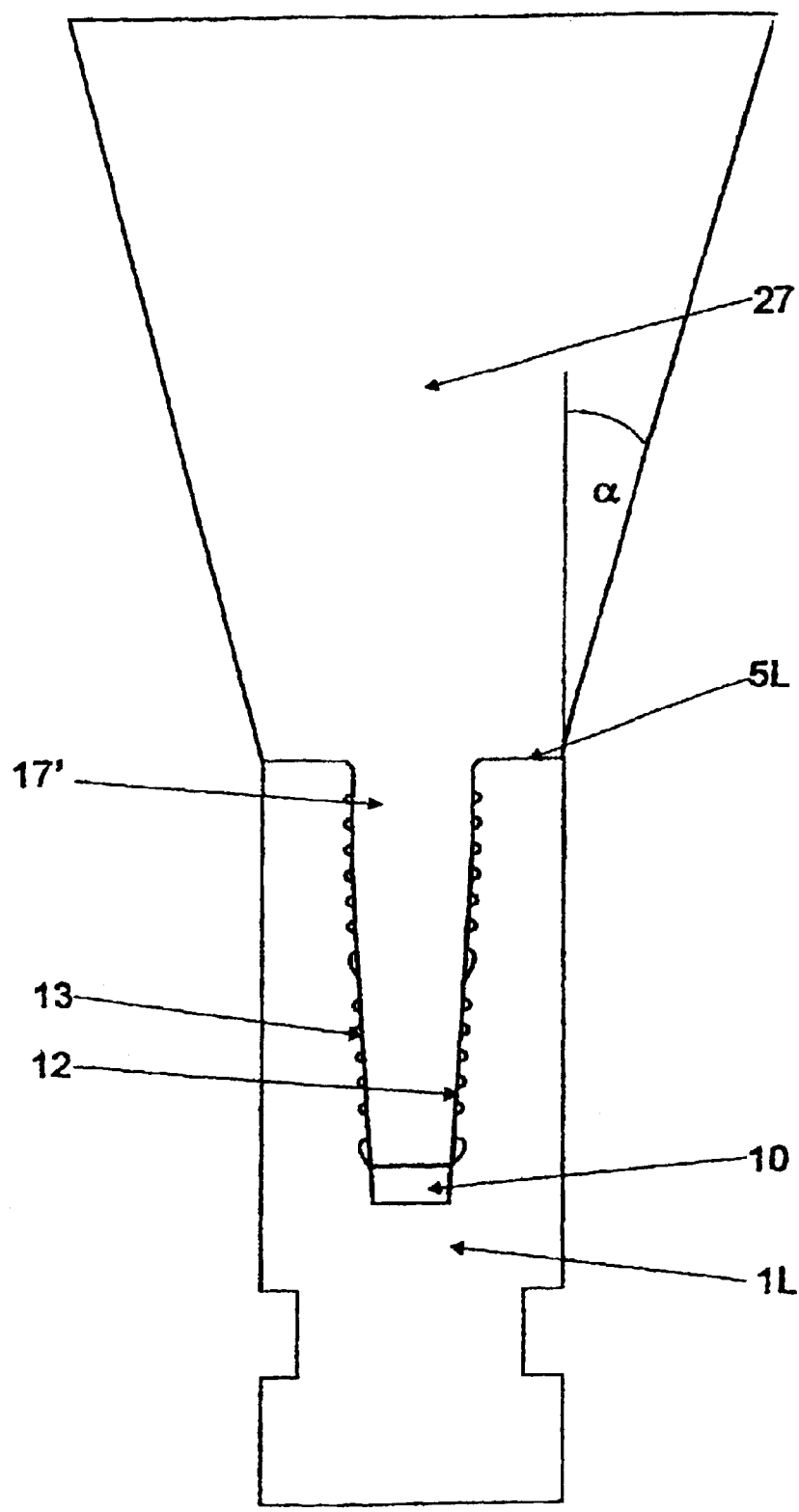
FIG. 13 As in FIG. 10, however of a final replacement tooth.
Figure 14:
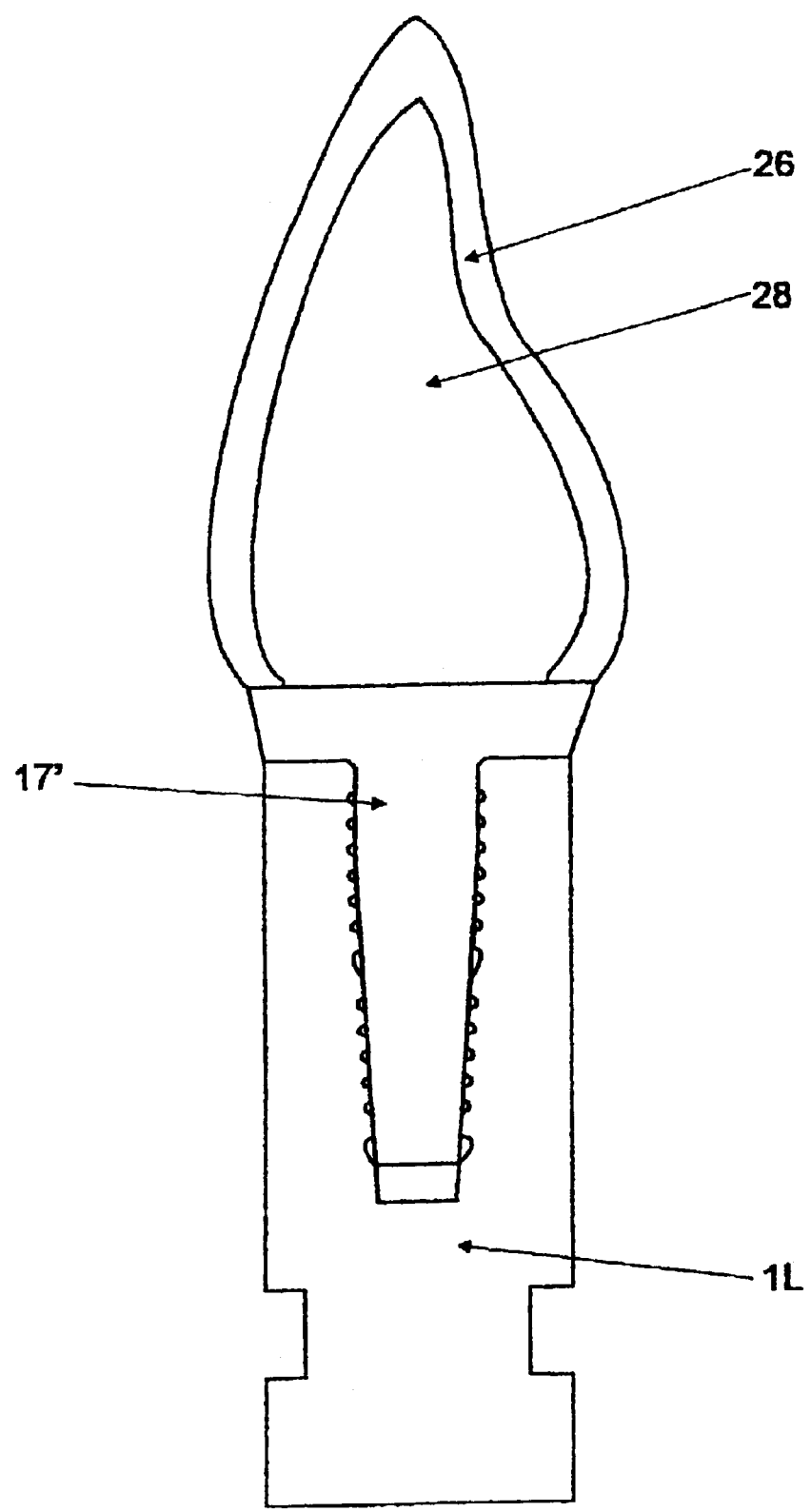
FIG. 14 As in FIG. 11, however of a final replacement tooth.

Like the temporary replacement tooth 25, this final replacement tooth 28 is produced from a blank 27 that is truncated in its head portion (FIG. 13), permitting a correction to slanted position in all directions in wide angular ranges. The connecting bridge 17' of the final replacement tooth 28 and/or its blank 27 do not contain any clip elements, but—apart from the rounded-off areas—it is adapted to the cross-sectional shape of the receiving recess 10 across the entire length of the connecting bridge 17'. Due to the ring grooves 13 in the wall 12 of the receiving recess 10, the connecting bridge 17 can be inserted without difficulty until the end face of the head portion of the blank 27 rests against the end face 5L of the lab implant 1L. Different starting areas of the "conical feature" ensure a non-positive connection via the contact surfaces 5 and 18 (see also FIG. 7). Proceeding from this installation position of the blank 27 in the lab implant 1L, the final shape of the replacement tooth 28, which in turn contains a ceramic layer 26 that has been burned on, can be prepared (FIG. 11).

The completion of this process consists of removing the final replacement tooth 28 from the lab implant 1L and inserting it into the implant 1 located in the jaw bone. In the assembled state, the two contact surfaces 5 and 18 rest non-positively against each other. A non-positive connection, which is formed with the help of adhesive or cement or is formed by clamping forces in the case of a shrinkage connection, exists also between the outer surface areas of the connecting bridge 17 and the wall 12 of the receiving recess 10.

Figure 15:
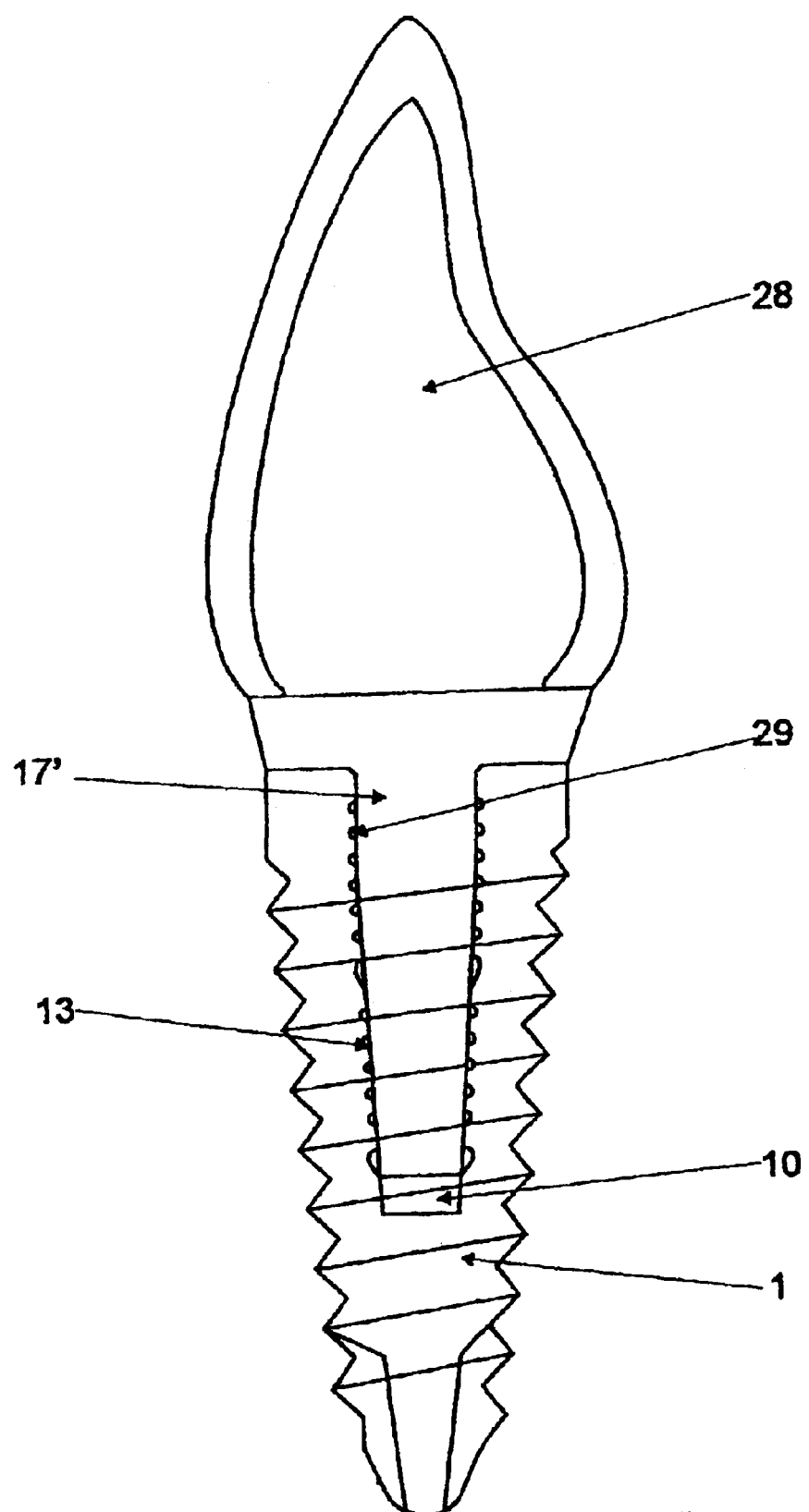
FIG. 15 As in FIG. 12, however of a final replacement tooth.

Pursuant to FIG. 15, the surface area 29 of the connecting bridge 17' and the contact surface 18 of the head portion are coated with a suitable adhesive or cement, which fills in the ring grooves 13 in the receiving recess 10 basically completely when inserting the connecting bridge 17'. After curing the adhesive, adhesive beads are thus created, which adhere to the connecting bridge 17' and establish a positive connection with the implant 1. Another positive connection exists via the contact surfaces 5 and 18, wherein the adhesive in this area is preferably applied in such a thin layer that only the surface roughness of the contact surfaces is filled in and there is still material contact between the adhesive and the implant/replacement tooth. Either way, adhesive should not protrude on the sides of the contact surfaces 5 and 18.

Figure 16:
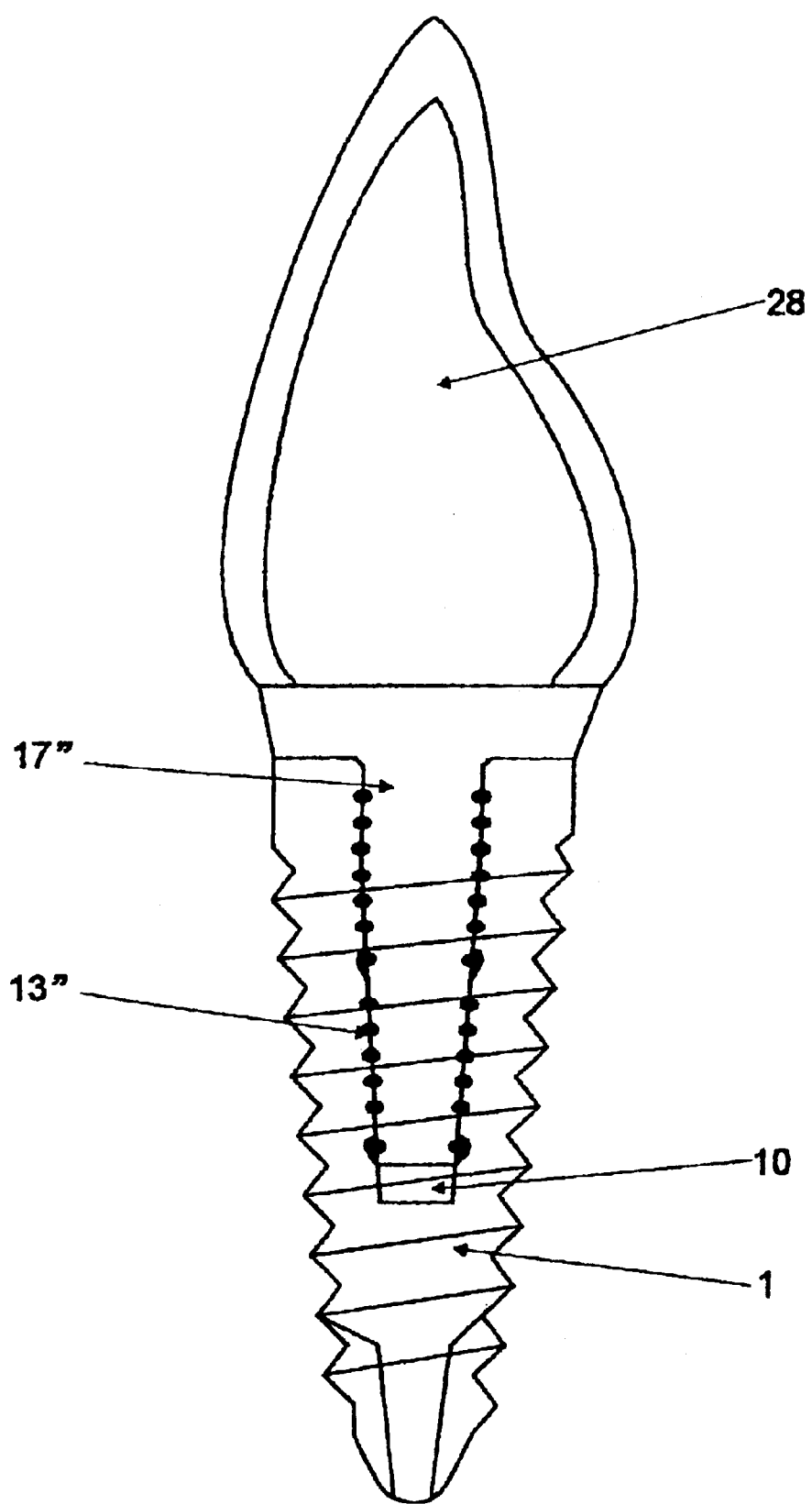
FIG. 16 As in FIG. 15, however with a connecting bridge with ring grooves in the surface area.

The stability of the connection between the replacement tooth 28 and the implant 1 can be further improved, even if in the surface area of the connecting bridge 17' a plurality of ring grooves 13" is incorporated, which correspond to the ring grooves 13 in the wall 12 of the receiving recess 10. Such a design is shown in FIG. 16. Here, adhesive rings, which are circular or oval in their cross-section, are formed, which establish a positive connection between the replacement tooth 28 and the implant 1.

What is claimed is:

1. Implant for receiving a connecting bridge of a medical device containing a head portion, comprising a longitudinal axis, a distal end, a proximal end and a top portion having a contact surface, whereby a receiving recess for the connecting bridge extends therefrom into implant, wherein the implant can be connected by its outer surface area to the inner surface area of a receiving bore hole in the bone of a human or animal body by force or adaptation, whereby connecting bridge, which is adapted to the receiving recess, can be anchored through clamping, shrinkage, adhesion or cementing, wherein in the anchored medical device rests in contact with the contact surface of the top portion protruding radially outward in its cross-section beyond the cross-section of the receiving recess on the proximal end of the implant across the entire surface against an allocated contact surface of the implant on its proximal end and the outer contour of the cross-section of the receiving recess at least in one section is not circular, wherein extending from the proximal end of the implant the receiving recess contains a cylindrical section, which is followed by a section that is tapered in its cross-section, and that extending from the head portion of the medical device the connecting bridge also contains a cylindrical section, which is followed by a section that is tapered in its cross-section; and wherein said implant in its anchored state between the connecting bridge and the wall of the receiving recess at least one ventilation duct is formed, which extends from a distal end face of the connecting bridge to the proximal end of the implant; and wherein for the contact surface of said implant at least one ventilation groove is incorporated, which extends from a ventilation duct to the surface area of the implant.

2. Implant pursuant to claim 1, wherein measured in the direction of the longitudinal axis of the implant the length of the cylindrical section of the connecting bridge is slightly less than the length of the cylindrical section of the receiving recess, also measured in the direction of the longitudinal axis of the implant.

3. Implant pursuant to claim 1, wherein the contact surface is circular and runs in a plane vertical to the longitudinal axis of the implant.

4. Implant pursuant to claim 1, wherein the wall of the receiving recess is equipped with a plurality of ring grooves, which each run in planes vertical to the longitudinal axis of the implant, or with a helical groove.

5. Implant pursuant to claim 1, wherein the wall of the receiving recess is equipped with at least one indentation, with which an elastic clip element of a medical device can positively engage.

6. Implant pursuant to claim 1, which is provided to receive a replacement tooth.

7. Implant for receiving a connecting bridge of a medical device containing a head portion, comprising a longitudinal axis, a distal end, proximal end and a top portion having a context surface, whereby a receiving recess for the connecting bridge extends therefrom into implant, wherein the implant can be connected by its outer surface area to the inner surface area of a receiving bore hole in the bone of a human or animal body by force or adaptation, whereby the connecting bridge, which is adapted to the receiving recess, can be anchored through clamping, shrinkage, adhesion or cementing, wherein in the anchored medical device rests in contact with the contact surface of the top portion protruding radially outward in its cross-section beyond the cross-section of the contact surface of the implant on its proximal end and the outer contour of the cross-section of the receiving recess at least in one section is not circular, wherein extending from the proximal end of the implant the receiving recess contains a cylindrical section, which is followed by a section that is tapered in its cross-section, and that extending from the head portion of the medical device the connecting bridge also contains a cylindrical section, which is followed by a section that is tapered in its cross-section; and wherein the vicinity of the proximal end of the implant the cross-section of the receiving recess takes on the shape of a rounded-off rectangle and in the vicinity of the its base it takes on the shape of a rounded-off square, wherein the transition between the above-described cross-sectional shapes is smooth.

8. Implant pursuant to claim 7, wherein a shorter edge length of the rectangle corresponds to an edge length of the square.

9. Medical device, which is received by the receiving recess of an implant, said receiving recess containing a wall, wherein said medical device rests on the contact surface of a head portion protruding radially outward in its cross-section beyond the cross-section of the receiving recess on the proximal end of the implant across the entire surface against an allocated contact surface of the implant on its proximal end, that the outer contour of the cross-section of the connecting bridge at least in one section is not circular, and that extending from a head portion the connecting bridge has a cylindrical section, which is followed by a section that is tapered in its cross-section; and wherein the vicinity of its proximal end the connecting bridge has a cross-section in the shape of a rectangle, the corners of which are rounded off or broken more than those of the rectangle of the cross-section of the receiving recess at the position allocated in the installed state, and that in the vicinity of its distal end it has a cross-section in the shape of a square, the corners of which are rounded off or broken more than those of the square of the cross-section of the receiving recess at the position allocated in the installed state.

10. Medical device pursuant to claim 9, wherein the distal end of the connecting bridge contains at least one axially protruding clip element, which in the assembled state can positively engage with an indentation in the receiving recess of an implant.

11. Medical device pursuant to claim 10, wherein a section, which in the assembled state is located outside the receiving recess, is equipped on its surface area with at least two opposing indentations.

12. Medical device pursuant to claim 11, wherein the indentations form a ring groove with a V-shaped cross-section.

13. Medical device pursuant to claim 9, which is a cap, a gingiva shaper, an impression rod and/or a replacement tooth.

14. Replacement tooth pursuant to claim 13, wherein the surface area of the connecting bridge is equipped with a plurality of ring grooves, which each run in a plane vertical to the longitudinal axis of the connecting bridge and in the anchored state of the replacement tooth correspond to the ring grooves in the wall of the receiving recess.

* * * * *